(12) United States Patent
    Segawa

(10) Patent No.: US 8,602,978 B2
(45) Date of Patent: Dec. 10, 2013

(54) TEMPERATURE CONTROL APPARATUS FOR ENDOSCOPE

(71) Applicant: Olympus Medical Systems Corp., Tokyo (JP)

(72) Inventor: Kazunori Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/650,520

(22) Filed: Oct. 12, 2012

(65) Prior Publication Data

US 2013/0116507 A1      May 9, 2013

Related U.S. Application Data

(63) Continuation of application No. PCT/JP2011/071382, filed on Sep. 20, 2011.

(30) Foreign Application Priority Data

Sep. 22, 2010   (JP) ................. 2010-212525

(51) Int. Cl.
    *A61B 1/00*          (2006.01)
(52) U.S. Cl.
    USPC ........................... 600/169; 600/103; 600/118
(58) Field of Classification Search
    USPC ................... 600/169, 103, 117, 118
    See application file for complete search history.

(56) References Cited

U.S. PATENT DOCUMENTS

| 4,031,898 | A * | 6/1977 | Hiltebrandt et al. ............ 606/31 |
| 4,402,311 | A * | 9/1983 | Hattori .......................... 600/117 |
| 7,938,774 | B2 * | 5/2011 | Segawa ......................... 600/169 |
| 2002/0045801 | A1 * | 4/2002 | Niida et al. ................... 600/118 |
| 2005/0103772 | A1 * | 5/2005 | Streit et al. ..................... 219/497 |
| 2007/0112255 | A1 * | 5/2007 | Ikeda et al. ................... 600/146 |
| 2007/0149856 | A1 * | 6/2007 | Segawa ......................... 600/169 |
| 2009/0112057 | A1 * | 4/2009 | Kammer et al. ............. 600/102 |

FOREIGN PATENT DOCUMENTS

| JP | 06-341656 | 12/1994 |
| JP | 2006-000282 | 1/2006 |
| JP | 1 803 388 A2 | 7/2007 |
| JP | 2007-175230 | 7/2007 |
| JP | 2009-261830 | 11/2009 |

* cited by examiner

*Primary Examiner* — John P Leubecker
(74) *Attorney, Agent, or Firm* — Scully, Scott, Murphy & Presser, P.C.

(57) ABSTRACT

A temperature control apparatus for an endoscope includes: a temperature detection section that detects a temperature of an object to be heated, the object to be heated being heated by a heater; a semiconductor switch that performs switching between supply and shut off of the power to the heater; a control section that controls the semiconductor switch to perform temperature control for the object to be heated, and performs heating stopping control to turn the semiconductor switch off; a mechanical switch that performs switching between continuity and shut off of a power line; and a heating stopping circuit that if an abnormality occurs in temperature control for the heater, performs heating stopping control to turn the mechanical switch off.

11 Claims, 7 Drawing Sheets

TEMPERATURE CONTROL APPARATUS FOR ENDOSCOPE

CROSS REFERENCE TO RELATED APPLICATION

This application is a continuation application of PCT/JP2011/071382 filed on Sep. 20, 2011 and claims benefit of Japanese Application No. 2010-212525 filed in Japan on Sep. 22, 2010, the entire contents of which are incorporated herein by this reference.

BACKGROUND OF THE INVENTION

1. Field of the Invention

The present invention relates to a temperature control apparatus for an endoscope, the temperature control apparatus controlling a temperature of a distal end of the endoscope.

2. Description of the Related Art

In recent years, endoscope apparatuses have been used in various fields such as, for example, a medical field and an industrial field. In the medical field, endoscope apparatuses are used for, for example, observation of an organ in a body cavity, a therapeutic treatment using a treatment instrument and surgical procedures under endoscopic observation.

In such medical field, an endoscope is inserted into the inside of a body, which has a temperature equal to a body temperature and is a highly humid environment. When an endoscope is inserted into such environment, fogging of a cover glass arranged at a distal end portion of the endoscope may occur. In order to prevent such fogging, it is necessary to heat up the cover glass before the cover glass is inserted into a body, which is inconvenient.

Therefore, Japanese Patent Application Laid-Open Publication No. 2007-175230 discloses an apparatus that heats up a cover glass at a distal end of an endoscope by means of a heater, and controls the heater by means of a temperature sensor that detects a temperature of the cover glass, to perform temperature control.

SUMMARY OF THE INVENTION

A temperature control apparatus for an endoscope according to an aspect of the present invention includes: a heater arranged in an endoscope, the heater being heated as a result of supply of power; a power line for supplying power generated by a power source to the heater, the power line being connected to the power source; a temperature detection section that detects a temperature of an object to be heated, the object to be heated being heated by the heater; a semiconductor switch provided on the power line, the semiconductor switch performing switching between supply and shut off of the power to the heater; a control section that controls the semiconductor switch according to a temperature detection result from the temperature detection section to perform temperature control for the object to be heated, and performs heating stopping control to turn the semiconductor switch off based on the temperature detection result; a mechanical switch provided on the power line, the mechanical switch performing switching between continuity and shut off of the line; and a heating stopping circuit that if an abnormality occurs in temperature control for the heater, performs heating stopping control to turn the mechanical switch off.

DETAILED DESCRIPTION OF THE PREFERRED EMBODIMENTS

Figure 1:
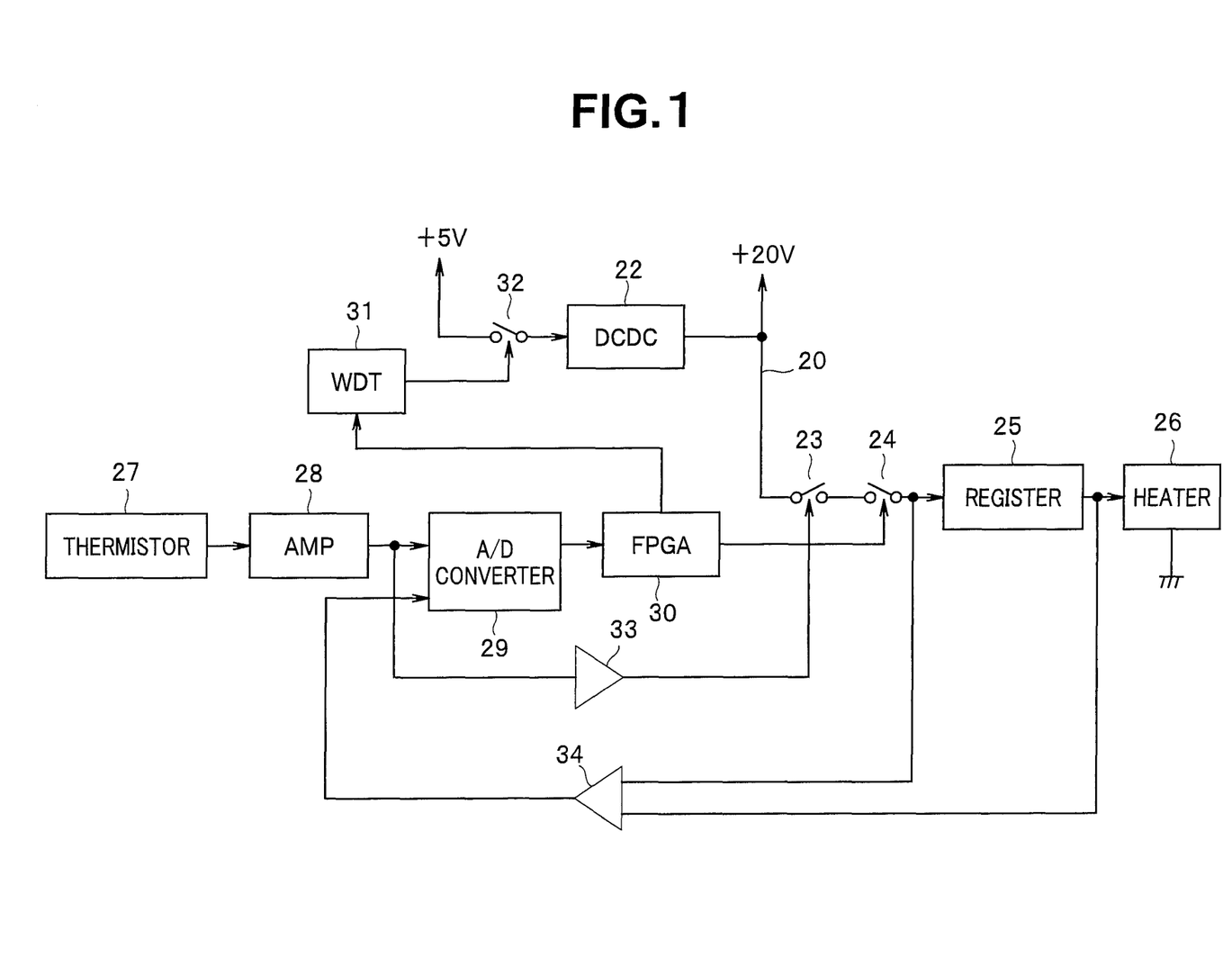
FIG. 1 is a block diagram illustrating a temperature control apparatus for an endoscope according to an embodiment of the present invention.
Figure 2:
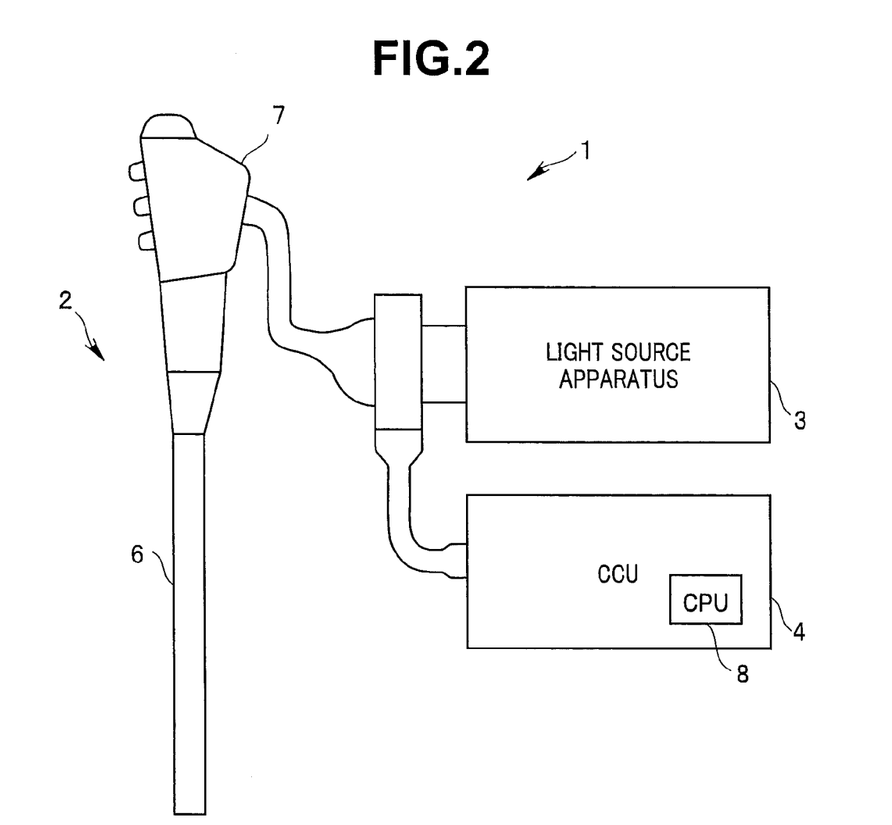
FIG. 2 is an outer appearance diagram illustrating a schematic configuration of an endoscope apparatus in which the temperature control apparatus for an endoscope in FIG. 1 is employed.

An embodiment of the present invention will be described below with reference to the drawings. FIG. 1 is a block diagram illustrating a temperature control apparatus for an endoscope according to an embodiment of the present invention. FIG. 2 is an outer appearance diagram illustrating a schematic configuration of an endoscope apparatus in which the temperature control apparatus for an endoscope in FIG. 1 is employed.

First, an overview of an endoscope apparatus will be described with reference to FIG. 2. As illustrated in FIG. 2, an endoscope apparatus 1 includes an endoscope 2, a light source apparatus 3 and a camera control unit (hereinafter, abbreviated as CCU) 4 that performs temperature control.

The endoscope 2 includes an insertion portion 6 to be inserted into an observation target, and an operation portion 7 connected to a proximal end portion of the insertion portion 6. The operation portion 7 is provided with switches for operating the endoscope 2, and is connected to the light source apparatus 3 and the CCU 4. The CCU 4 includes various apparatuses including a CPU 8 and circuits inside.

Observation using the endoscope apparatus 1 is performed by inserting the insertion portion 6 of the endoscope 2 into a human body. In this case, for example, a non-illustrated trocar may be arranged so as to pass through an abdominal wall of a human body in order to guide the insertion portion 6 to a desired observation site by inserting the insertion portion 6 into the trocar.

Inside the insertion portion 6, a light guide, which will be described later, is inserted, enabling the observation site to be illuminated by illuminating light from the light source apparatus 3. Furthermore, image pickup means is arranged at a distal end portion of the insertion portion 6, and the image pickup device picks up light reflected from the observation site, based on the control performed by the CCU 4.

The CCU 4 operates by means of the various apparatuses including the CPU 8 and circuits, and performs processing of a picked-up image, and the processed image is outputted to, for example, a non-illustrated monitor and displayed.

Next, a detailed configuration of the insertion portion 6 will be described with reference to FIG. 3.

Figure 3:
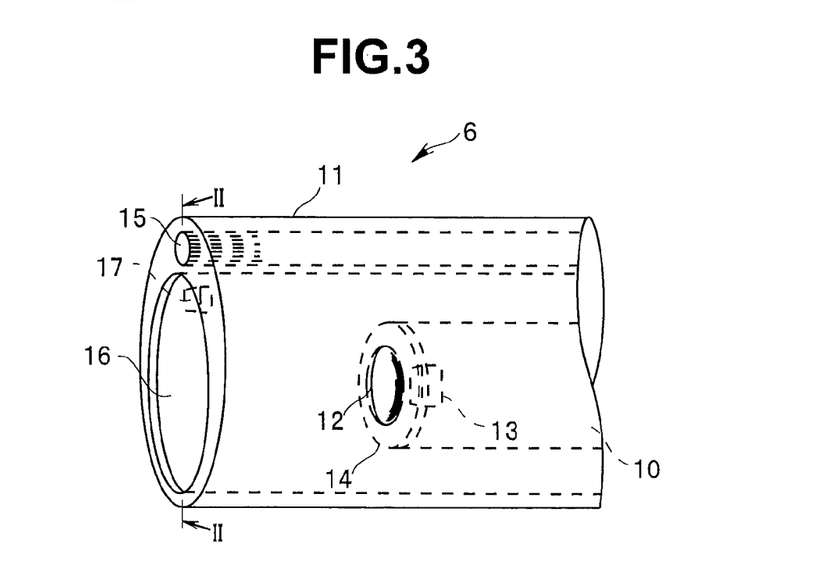
FIG. 3 is a diagram of a schematic configuration of an insertion portion 6.

FIG. 3 is a diagram of a schematic configuration of the insertion portion 6. As illustrated in FIG. 3, the insertion portion 6 includes an inner tube 10, and an outer tube 11 arranged so as to cover an outer circumferential face of the inner tube 10, the outer tube 11 having a diameter larger than that of the inner tube 10. Since the outer tube 11 may directly touch a living tissue, the inner tube 10 and the outer tube 11 each include an insulating material.

Furthermore, as illustrated in FIG. 3, the inner tube 10 includes a lens 12, a charge-coupled device (hereinafter, abbreviated as CCD) 13 composing an image pickup section, and a heater 14 that provides a heat-generating section. The heater 14 has a ring shape, and is arranged so that an outer circumferential face of the ring shape extends along an inner wall surface of the distal end portion of the inner tube 10.

The lens 12 is arranged on the inner circumferential side of the ring-shaped heater 14 at the distal end portion of the inner tube 10. Furthermore, the CCD 13 is arranged so that a light-receiving surface is located at a position where light from the outside is formed inside the inner tube 10 via the lens 12.

Into the outer tube 11, a light guide 15, which includes light guide fibers, is inserted along an axis direction of the outer tube 11, and a distal end of the light guide 15 is exposed at a distal end face of the outer tube 11. Furthermore, at a distal end portion of the outer tube 11, a disk-shaped cover glass 16 including a member that transmits light is arranged.

A temperature sensor 17, which is a temperature detection section, is arranged so as to be in contact with an inner face of the cover glass 16 that faces the lens 12. For the temperature sensor 17, for example, a thermistor can be employed. For correct temperature detection, the temperature sensor 17 is favorably arranged in the vicinity of the cover glass 16. Note that the cover glass 16 may be composed of a lens. Furthermore, a light-emitting diode may be provided at the distal end portion of the insertion portion 6 without provision of the light guide 15.

Figure 4:
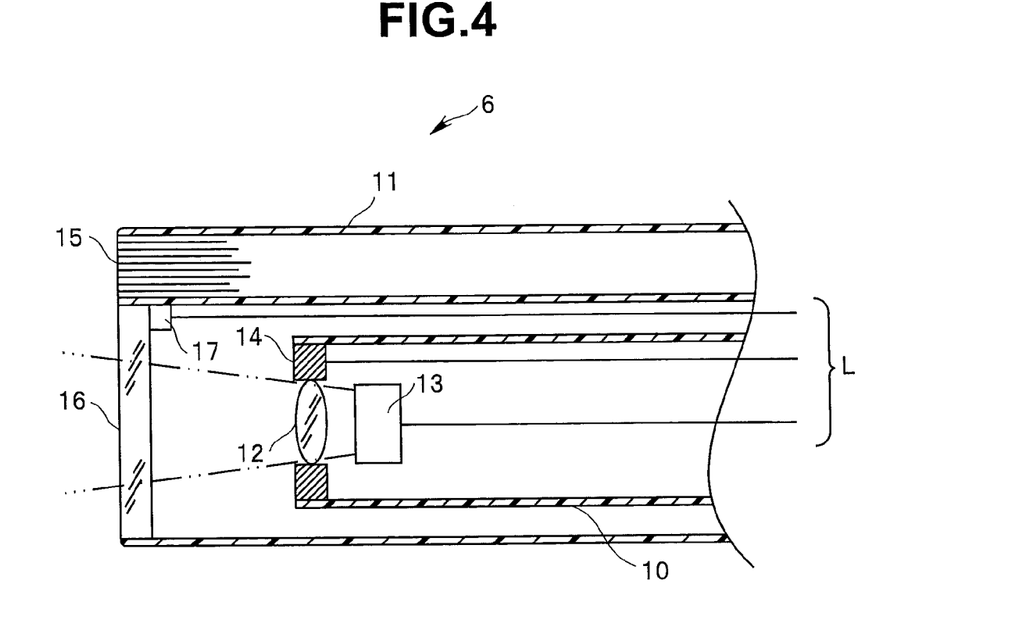
FIG. 4 is a schematic cross-sectional diagram along line II-II of FIG. 3.

A further detailed configuration of the insertion portion 6 will be described below with reference to a cross-sectional diagram.

FIG. 4 is a schematic cross-sectional diagram along the line II-II in FIG. 3. As illustrated in FIG. 4, each of the CCD 13, the heater 14 and the temperature sensor 17 is connected to the CCU 4 via a signal line L. Each of the heater 14 and the temperature sensor 17 is arranged at a position where an image pickup range for the CCD 13 is not included (in the figure, the image pickup range is indicated by alternate long and two short dashed lines).

Note that the position and the shape of the heater 14 are not limited to the position and the shape described above, and may be any position and have any shape as long as the heater 14 is arranged between the distal end portion of the inner tube 10 and the facing surface of the facing cover glass 16 so as not to be included in the image pickup range for the CCD 13.

As described above, illuminating light generated in the light source apparatus 3 is guided by the light guide 15, and exits from the distal end of the insertion portion 6, that is, the distal end of the outer tube 11. Light reflected from the illuminated observation site passes through the cover glass 16 and forms an image on the light-receiving surface of the CCD 13 via the lens 12. The CCD 13, which is controlled by the CCU 4, picks up the formed image to output an image pickup signal to the CCU 4.

Furthermore, the heater 14 and the temperature sensor 17 are elements for preventing fogging of the cover glass 16 occurring when the insertion portion 6 is inserted into a human body. The heater 14 generates heat as a result of a voltage being applied thereto by the CCU 4, and heats up the cover glass 16.

A temperature of the cover glass 16 is detected by the temperature sensor 17. For example, a resistance value of the temperature sensor 17 changes according to the temperature, and the resistance value is constantly detected by the CCU 4. A voltage applied to the heater 14 according to the detected temperature is controlled by the CCU 4 so that the temperature of the cover glass 16 becomes a predetermined temperature.

In FIG. 1, a heater 26 and a thermistor 27 correspond to the heater 14 and the temperature sensor 17 in FIGS. 3 and 4. In other words, the heater 26 and the thermistor 27 in the temperature control apparatus for an endoscope illustrated in FIG. 1 is incorporated in the endoscope 2. The other components in FIG. 1 are incorporated in the CCU 4.

A power-supply voltage of, for example, +20 V is supplied to the heater 26 via switches 23 and 24 and a register 25 provided on a power line 20. Note that the switch 23 is a mechanical relay and the switch 24 is a semiconductor switch such as a MOS switch. A DC/DC converter (hereinafter, abbreviated as DC/DC) 22 is provided with a power-supply voltage of +5 V from a power source via a switch 32, and the DC/DC 22 converts the power-supply voltage into, for example, +20 V and supplies the voltage to the power line 20.

One end of the heater 26 is connected to the register 25 and the other end of the heater 26 is connected to a reference potential point. When the switches 32, 23 and 24 are on, the power-supply voltage of +20 V is supplied to the heater 26 via the register 25, whereby the heater 26 is heated. An FPGA 30 controls a temperature of the heater 26 by performing on/off control of the switch 24.

As described above, the thermistor 27 exhibits a resistance value according to the temperature of the cover glass 16. An AMP 28 generates a voltage according to the resistance value of the thermistor 27 and outputs the voltage to an A/D converter 29. The A/D converter 29 converts an input analog value into a digital signal and outputs the digital signal to the FPGA 30. In this way, the FPGA 30 is provided with a result of detection of the temperature of the cover glass 16. The FPGA 30 performs the on/off control of the switch 24 so that the result of detection of the temperature is a value within a predetermined range.

Figure 5:
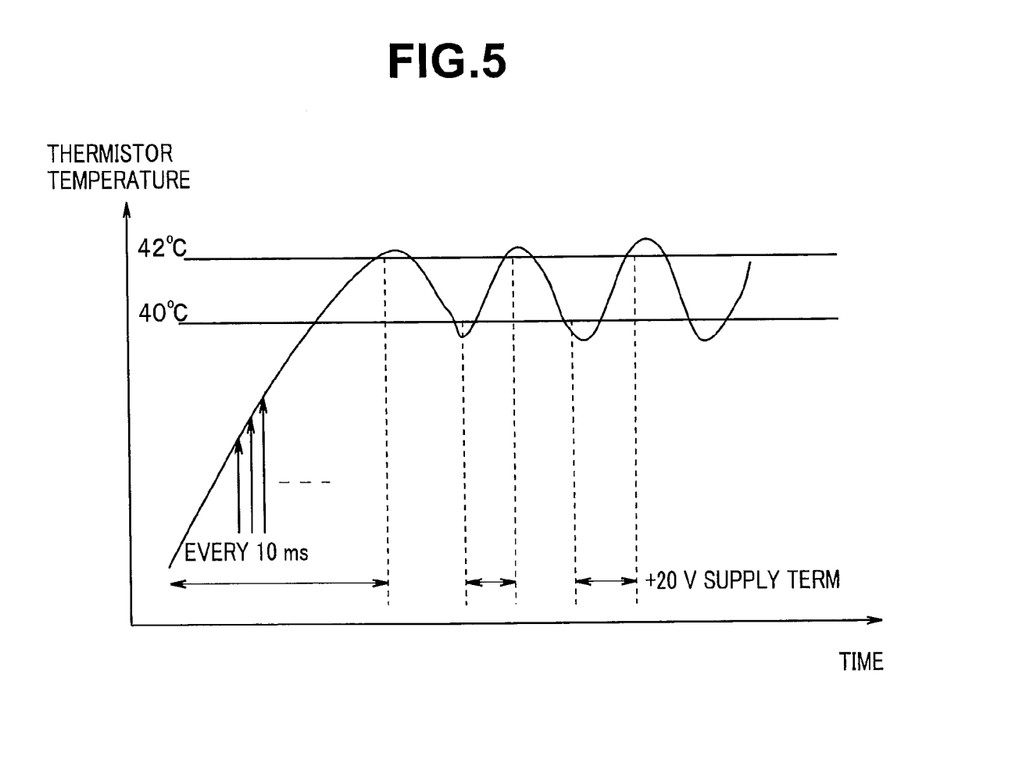
FIG. 5 is a graph illustrating temperature control performed by an FPGA 30 with time as the abscissa axis and temperature of a thermistor 27 as the ordinate axis.

FIG. 5 is a graph for illustrating temperature control performed by the FPGA 30 with time as the abscissa axis and detected temperature of the thermistor 27 as the ordinate axis.

When a surgical procedure is conducted using an endoscope apparatus, fogging may occur on a cover glass 16 arranged at a distal end portion of an insertion portion of an endoscope. Therefore, the fogging is prevented by maintaining the cover glass 16 at a range of temperatures that is higher than a body temperature and causes no thermal damage of a living tissue, for example, no less than 38° C. and no more than 42° C.

The FPGA 30, for example, performs the on/off control of the switch 24 every 10 ms based on the result of detection of the temperature of the cover glass 16. After the FPGA 30 starts heating the heater 26, the FPGA 30 detects the temperature every 10 ms. If the detected temperature exceeds 42° C., the FPGA 30 turns the switch 24 off. Consequently, supply of the power-supply voltage to the heater 26 is stopped. Then, an increase in temperature of the heater 26 is stopped and the temperature of the heater 26 starts decreasing. If the temperature sensed by the thermistor 27 becomes 40° C. or below as a result of that, the FPGA 30 turns the switch 24 on again. Consequently, supply of the power-supply voltage to the heater 26 is resumed, and the temperature of the heater 26 increases.

The FPGA 30 repeats operation similar to the above thereafter to perform temperature control so that the sensed temperature becomes substantially a temperature between 40° C. and 42° C.

In the present embodiment, when the FPGA 30 senses a failure in any of the respective components, the FPGA 30 turns the switch 24 off. In other words, the switch 24 has a function that shuts off supply of the power-supply voltage for temperature control, as well as a function of a heating stopping switch that stops power supply to the heater 26 at the time of a failure of a component.

The switch 24 is repeatedly turned on/off relatively frequently for temperature control. Accordingly, considering the tolerance for turning-on/off, it is necessary to use a semiconductor switch for the switch 24. However, the semiconductor switch enters a shorted state at the time of a failure. In other words, when the switch 24 fails, the switch 24 cannot be turned off by the FPGA 30, resulting in impossibility to stop power supply to the heater 26.

Therefore, in the present embodiment, the switch 23 is arranged in series to the switch 24 on the power line 20. A mechanical relay, which enters an open state at the time of a failure, is used for the switch 23 to reliably stop power supply to the heater 26 at the time of a failure of the switch 24, enabling prevention of excessive heating of the heater 26.

Furthermore, in the present embodiment, the switch 32, which is a mechanical relay, is arranged on the input end side of the DC/DC 22 that supplies the power-supply voltage to the power line 20. The switch 32 is turned off to stop supply of the power-supply voltage from the DC/DC 22, enabling prevention of excessive heating of the heater 26 at the time of a failure of the switch 24.

In the present embodiment, on/off control of the switch 23 is performed by a comparator 33. The comparator 33 is provided with an output of the AMP 28. The comparator 33 compares the output of the AMP 28 and a predetermined threshold voltage, and if the output of the AMP 28 exceeds the threshold voltage, the switch 23 is turned off. Consequently, it is possible to, if an abnormal voltage value from the AMP 28 appears, turn the switch 23 off, enabling the heater 26 to be prevented from entering an excessively-heated state.

Figure 7:
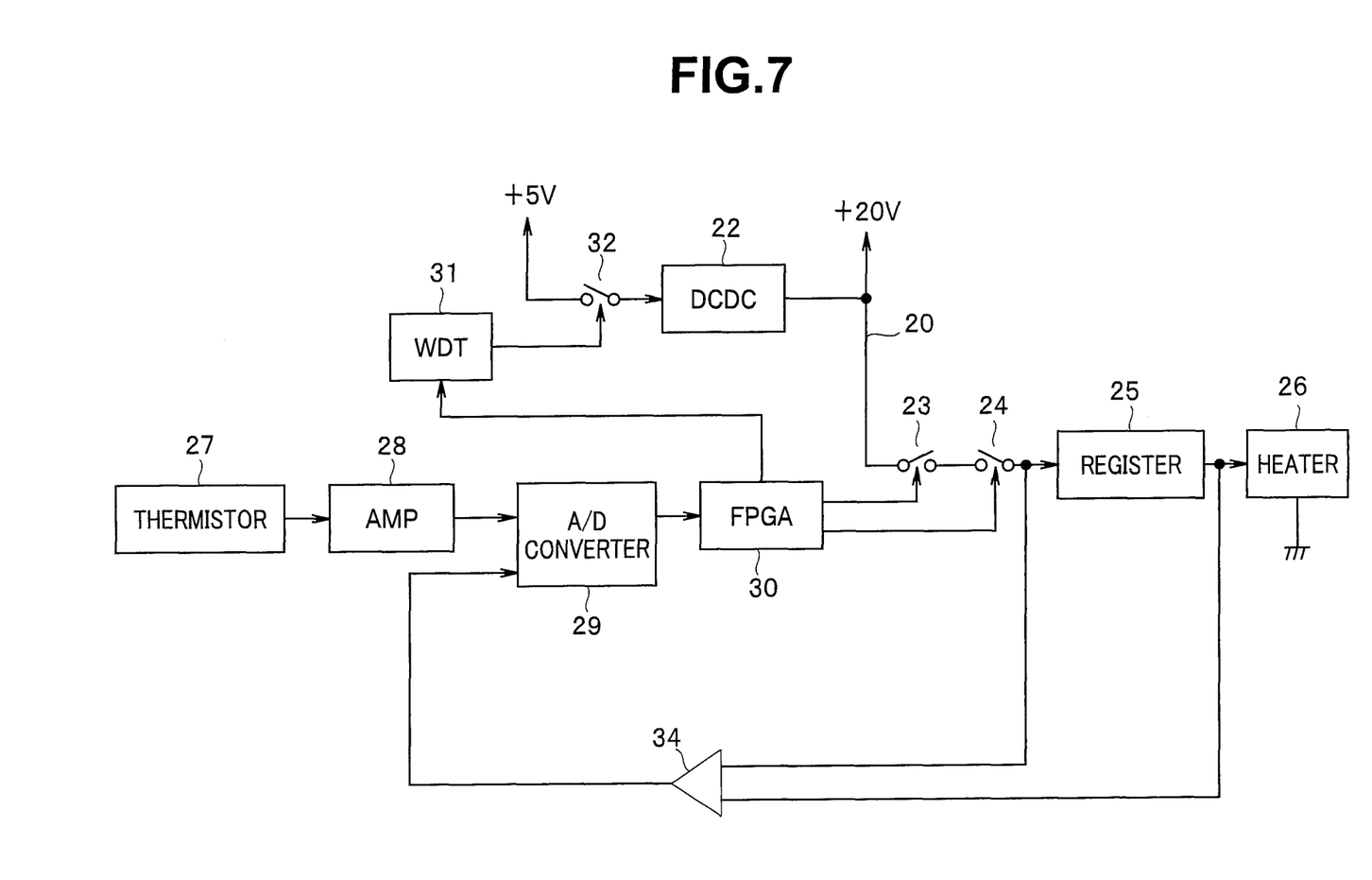
FIG. 7 is a block diagram illustrating a modification.

Note that although the present embodiment is described in terms of an example in which the on/off control of the switch 23 is performed by the comparator 33, as illustrated in FIG. 7, the on/off control of the switch 23 may be performed by the FPGA 30.

Figure 8:
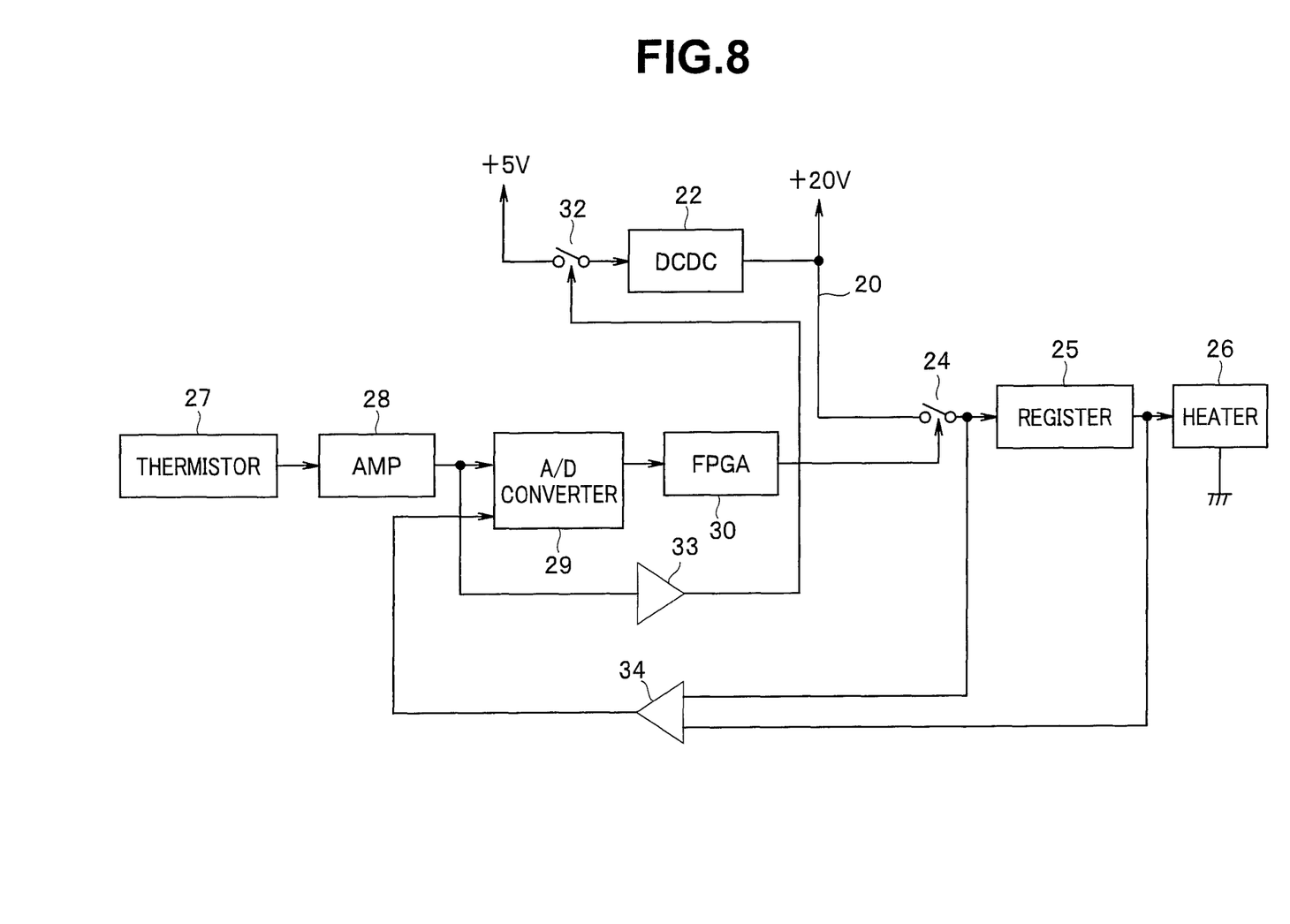
FIG. 8 is a block diagram illustrating a modification.

Furthermore, although an example in which the comparator 33 performs the on/off control of the switch 23 is described, as illustrated in FIG. 8, the comparator 33 may perform the on/off control of the switch 32.

Furthermore, in the present embodiment, on/off control of the switch 32 is performed by a watchdog timer (hereinafter, referred to as WDT) 31. The WDT 31 is supplied with clocks from the FPGA 30, and the WDT 31 detects, e.g., an abnormality of the FPGA 30 from stoppage of the supply of clocks from the FPGA 30. When the supply of clocks from the FPGA 30 is stopped, the WDT 31 turns the switch 32 off. Consequently, when an abnormality occurs in the FPGA 30, the switch 32 can be turned off, enabling the heater 26 to be prevented from entering an excessively-heated state.

Figure 9:
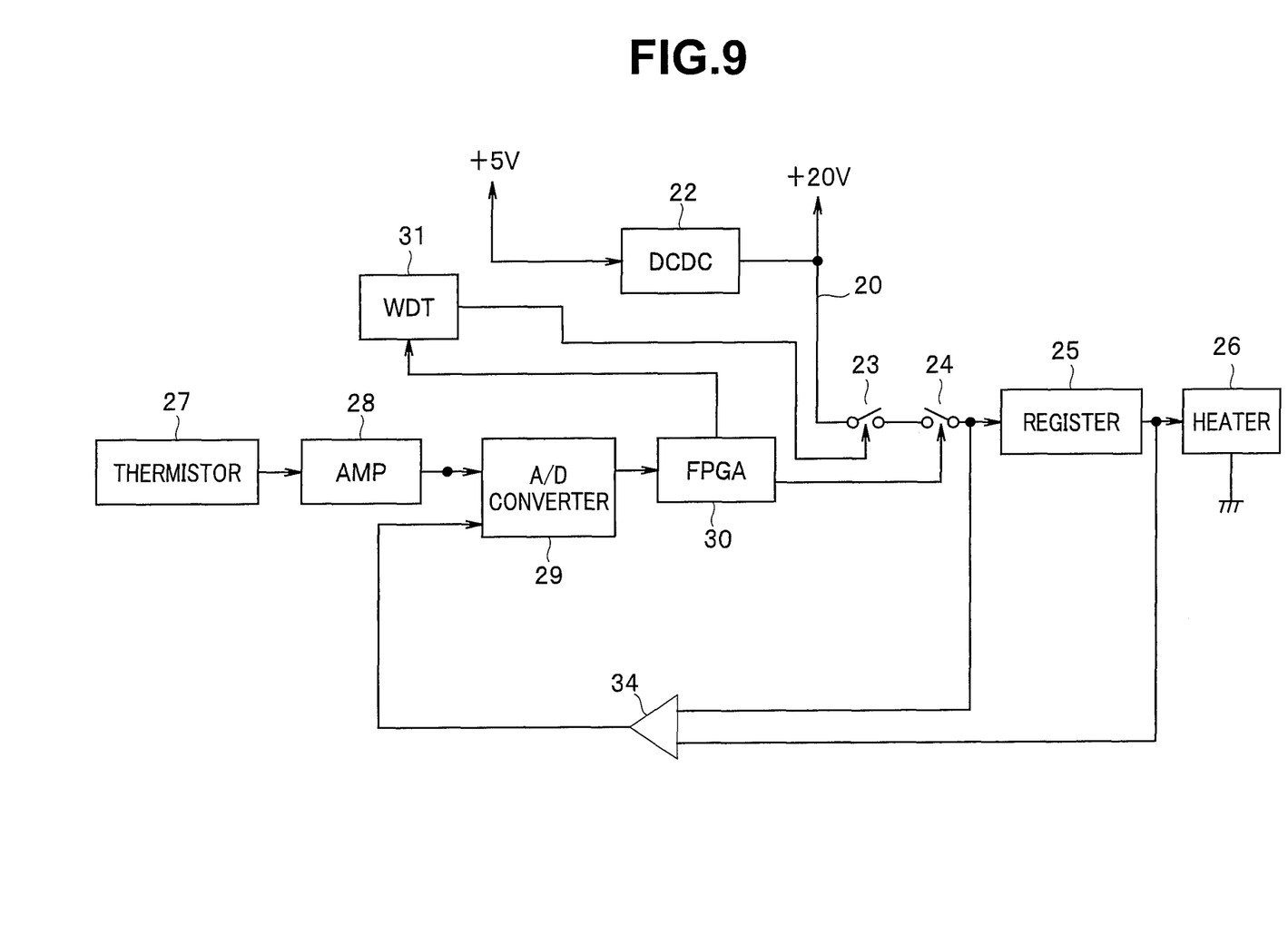
FIG. 9 is a block diagram illustrating a modification.

Note that although the present embodiment is described in terms of an example in which the WDT 31 performs the on/off control of the switch 32, as illustrated in FIG. 9, the WDT 31 may perform the on/off control of the switch 23.

Furthermore, in the present embodiment, voltages at input and output ends of the register 25 are supplied to an operational amplifier 34. The operational amplifier 34 calculates a difference between the voltages of the input and output ends of the register 25 to detect a current flowing in the power line 20. The operational amplifier 34 outputs an output based on a value of the detected current to the A/D converter 29. The A/D converter 29 provides the current detected by the operational amplifier 34 to the FPGA 30. If the FPGA 30 determines that there is an abnormality in the current detected by the operational amplifier 34, the FPGA 30 turns the switch 24 off and stops the supply of clocks to the WDT 31. Note that the A/D converter 29 time-divisionally loads the output of the AMP 28 and the output of the operational amplifier 34, converts the outputs into digital signals and outputs the digital signals.

Figure 6:
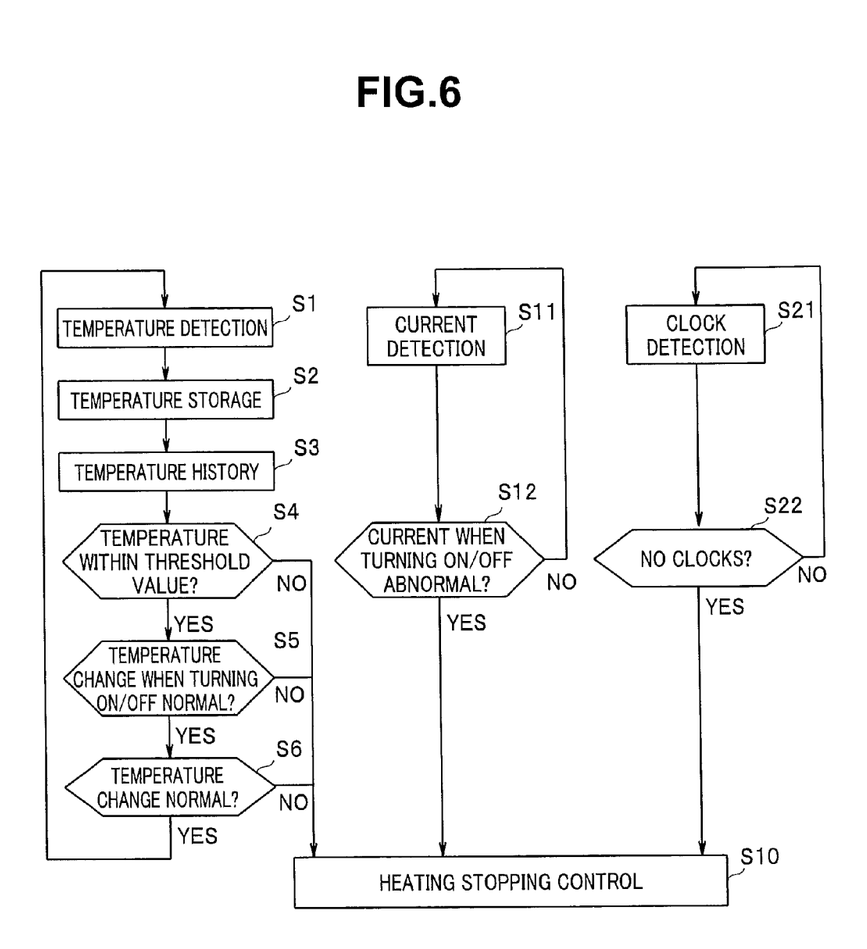
FIG. 6 is a flowchart for illustrating failures of respective components and control at the time of each of the failures.

Next, failures in the respective components and control at the time of each of the failures will be described with reference to the flowchart in FIG. 6.

The switches 23 and 32 each include a mechanical relay, and are normally on. Accordingly, normally, the power-supply voltage is supplied to the DC/DC 22, and the DC/DC 20 supplies +20 V to the power line. Since the switch 23 is normally on, when the switch 24 is on, the voltage of +20 V in the power line 20 is applied to the heater 26 via the register 25, and when the switch 24 is off, the voltage of +20 V is not applied to the heater 26.

The thermistor 27 detects a temperature of the cover glass 16 in step S1. Also, the operational amplifier 34 detects a current flowing in the register 25 in step S11. Also, the WDT 31 monitors clocks outputted by the FPGA 30 in step S21.

An output of the thermistor 27 is amplified by the AMP 28 and converted into a digital signal by the A/D converter 29, and then supplied to the FPGA 30. The FPGA 30 stores the temperature detection result (step S2) and monitors a history of temperature detection results (step S3).

(1) Failure of the Thermistor 27

The thermistor 27 may come into an open state or a shorted state by a failure of the thermistor 27. For example, the thermistor 27 or a cable connected to the thermistor 27 may be disconnected by, e.g., a mechanical impact. In this case, an output of the AMP 28 and an output of the A/D converter 29 each become a predetermined upper limit value or lower limit value according to the open or shorted state of the thermistor 27. If the output of the A/D converter 29 becomes the predetermined upper limit value or lower limit value, the FPGA 30 determines that the thermistor 27 fails (step S4) and turns the switch 24 off. Consequently, heating of the heater 26 is stopped (step S10).

(2) Failure of the Heater 26

The heater 26 may come into an open state or a shorted state by a failure of the heater 26. When the heater 26 is open, no current flows to the reference potential point from the power line 20 via the heater 26. Accordingly, no current flows in the register 25. The operational amplifier 34 detects that no voltage drop occurs in the register 25, and outputs the detection result to the A/D converter 29. The A/D converter 29 outputs the output of the operational amplifier 34 to the FPGA 30. If no current flows in the register 25 during the switch 24 being on, the FPGA 30 determines in step S12 that the heater 26 fails, and turns the switch 24 off.

Also, if the heater 26 enters a shorted state, a current different from that of a case where the heater 26 is normal flows in the register 25. The operational amplifier 34 detects the current flowing in the register 25, and outputs the detection result to the A/D converter 29. The FPGA 30 determines that the heater 26 is in a shorted state, according to the result of detection of the current flowing in the register 25 (step S12), and thereafter turns the switch 24 off.

(3) Failure of the Switch 24 (MOS Switch)

When the switch 24 fails, the switch 24 enters a shorted state. Normally, the switch 23 is also on and a current constantly flows in the register 25. The current is detected by the operational amplifier 34 and the detection result is supplied to the FPGA 30 via the A/D converter 29. If the FPGA 30 detects that a current flows in the register 25 during the switch 24 being controlled to be off, the FPGA 30 determines that the switch 24 fails (step S12) and stops supply of clocks to the WDT 31.

If the supply of clocks from the FPGA 30 is stopped (step S22), the WDT 31 turns the switch 32 off. Consequently, power supply to the DC/DC 22 is stopped and the DC/DC 22 stops supply of a voltage of +20 V to the power line 20. Consequently, the heating of the heater 26 is prevented and leakage of current is also prevented (step S10).

Note that although in the present embodiment, at the time of a failure of the switch 24, the switch 32 is turned off to prevent heating of the heater 26, it is clear that a configuration may also be made so that the switch 23 is turned off by an output of the FPGA 30.

(4) Failure of the Switch 23 (Mechanical Relay)

The switch 23 becomes open when the switch 23 fails. Accordingly, even if the switch 23 fails, the heater 26 is merely not heated. Accordingly, the present embodiment does not respond to a failure of the switch 23.

(5) Failure of, e.g., the AMP 28

A temperature of the heater 26 may increase beyond a predetermined threshold value owing to, e.g., a failure of the switch 24. The comparator 33 detects whether or not an output of the AMP 28 exceeds the predetermined threshold voltage (step S4), and if the output exceeds the predetermined threshold voltage, the comparator 33 provides an output to turn the switch 23 off. Heating of the heater 26 is stopped by the control performed by the comparator 33 as described above (step S10), enabling prevention of an abnormal increase in temperature of the heater 26.

Where the AMP 28 fails, a high voltage may be outputted from the AMP 28 even though a temperature detected by the thermistor 27 is low. In such case, the switch 23 can be turned off by the comparator 33, and thus, no problem occurs.

However, conversely, a low voltage relative to the temperature detected by the thermistor 27 may be outputted from the AMP 28 owning to a failure of the AMP 28. In such case, the switch 23 cannot be turned off by the comparator 33. However, even in such case, the FPGA 30 stores a relationship between a state of the switch 24 and a detected temperature from the A/D converter 29, and if the detected temperature does not increase to a predetermined temperature even if the switch 24 is successively on for a predetermined period of time, the FPGA 30 can determine that, e.g., the AMP 28 and/or the A/D converter 29 fails (step S6). If the FPGA 30 detects a failure of the AMP 28 and/or the A/D converter 29, the FPGA 30 turns the switch 24 off.

(6) Failure of the FPGA 30

A failure of the FPGA 30 can be detected by the WDT 31. When the WDT 31 detects the failure from stoppage of supply of clocks from the FPGA 30 (step S22), the WDT 31 turns the switch 32 off. Consequently, heating of the heater 26 is prevented (step S10).

(7) Dropping the Heater 26 or the Thermistor 27 Off from the Vicinity of the Cover Glass 16

For example, when the thermistor 27 drops off from a position where the thermistor 27 should be attached, the thermistor 27 may be unable to sufficiently detect a temperature of the cover glass 16 depending on the site where the thermistor 27 dropped off, resulting in provision of a setting that makes a temperature of the heater 26 be unnecessarily increased. Normally, when the switch 24 is on, a voltage is applied to the heater 26, whereby the heater 26 is heated, and thus the temperature of the thermistor 27 can be considered to necessarily increase. The FPGA 30 loads a temperature detection result from the thermistor 27, for example, at 10 ms intervals to perform on/off control of the switch 24, and determines whether or not the detected temperature increases by an increase according to the interval (step S5). If an expected temperature increase cannot be detected, the FPGA 30 presumes that such failure of expected temperature increase is due to, e.g., dropping-off of the thermistor 27 or a failure caused by autoclaving.

If no expected temperature increase occurs during the switch 24 being controlled to be on, the FPGA 30 determines that there is an abnormality such as dropping-off, and turns the switch 24 off. Consequently, the heater 26 can be prevented from being abnormally heated as a result of an abnormality such as dropping-off of the thermistor 27 (step S10).

As described above, in the present embodiment, on/off control of a semiconductor switch is performed based on a detected temperature of a cover glass to perform temperature control for a heater. In this case, if an FPGA detects an abnormality, the FPGA performs a heating stopping operation to turn the semiconductor switch off. Furthermore, in the present embodiment, considering the fact that if a semiconductor switch fails, the semiconductor switch enters a shorted state, mechanical switches such as mechanical relays are provided on a power line or a power supply line, and the switches are controlled by the FPGA or other components to reliably prevent excessive heating of the heater. Consequently, in the present embodiment, while fogging of the cover glass is prevented, even if a failure occurs in a single component, heating stopping control is performed, enabling maintenance of a safe temperature.

What is claimed is:

1. A temperature control apparatus for an endoscope, the temperature control apparatus comprising:
    a heater arranged in an endoscope, the heater being heated as a result of supply of power;
    a power line for supplying power generated by a power source to the heater, the power line being connected to the power source;
    a temperature detection section that detects a temperature of an object to be heated, the object to be heated being heated by the heater;
    a semiconductor switch provided on the power line, the semiconductor switch performing switching between supply and shut off of the power to the heater;
    a control section that controls the semiconductor switch according to a temperature detection result from the temperature detection section to perform temperature control for the object to be heated, and performs heating stopping control to turn the semiconductor switch off based on the temperature detection result;
    a mechanical switch provided on the power line, the mechanical switch performing switching between continuity and shut off of the line; and
    a heating stopping circuit that if an abnormality occurs in temperature control for the heater, performs heating stopping control to turn the mechanical switch off.

2. The temperature control apparatus for an endoscope according to claim 1, wherein the heating stopping circuit detects at least a failure of the semiconductor switch, and performs the heating stopping control to turn the mechanical switch off.

3. The temperature control apparatus for an endoscope according to claim 1, wherein if the heating stopping circuit detects based on the temperature detection result that the temperature of the object to be heated becomes a high temperature equal to or exceeding a predetermined threshold value, the heating stopping circuit performs the heating stopping control to turn the mechanical switch off.

4. The temperature control apparatus for an endoscope according to claim 1, comprising a control section monitoring circuit that detects a failure in the control section and performs the heating stopping control to turn the mechanical switch off.

5. The temperature control apparatus for an endoscope according to claim 1, wherein if the control section detects based on the temperature detection result that the temperature of the object to the heated becomes a high temperature equal to or exceeding a predetermined threshold value, the control section performs the heating stopping control to turn the semiconductor switch off.

6. The temperature control apparatus for an endoscope according to claim 1, wherein if the control section detects based on the temperature detection result an abnormality of at least one of the temperature detection section and the heater, the control section performs the heating stopping control to turn the semiconductor switch off.

7. The temperature control apparatus for an endoscope according to claim 1,
   wherein the heating stopping circuit is provided by a function of a part of the control section; and
   wherein the heating stopping circuit detects at least a failure of the semiconductor switch, and performs the heating stopping control to turn the mechanical switch off.

8. The temperature control apparatus for an endoscope according to claim 1, wherein the heating stopping circuit includes:
   a current detection section that detects a current flowing in the power line; and
   a switch control section that performs on/off control of the mechanical switch according to the detection result from the current detection section.

9. The temperature control apparatus for an endoscope according to claim 1, wherein the mechanical switch includes a mechanical relay.

10. The temperature control apparatus for an endoscope according to claim 1, wherein the semiconductor switch includes a MOS switch.

11. The endoscope temperature control apparatus according to claim 1, wherein the mechanical switch is provided on the power line, between the power source and a power circuit that generates power to be supplied to the heater
   a switch control section provided by a function of a part of the control section, the switch control section performing on/off control of the mechanical switch according to a detection result from the current detection section.

* * * * *